(12) United States Patent
Kim et al.

(10) Patent No.: US 12,703,683 B2
(45) Date of Patent: Aug. 11, 2026

(54) CRYSTALLINE FORM III OF MELANOCORTIN RECEPTOR AGONIST COMPOUND AND PREPARATION METHOD THEREFOR

(71) Applicant: LG CHEM, LTD., Seoul (KR)

(72) Inventors: Ji Yoon Kim, Daejeon (KR); Seul Ah Chun, Daejeon (KR); Sung Won Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 348 days.

(21) Appl. No.: 18/258,730

(22) PCT Filed: Dec. 22, 2021

(86) PCT No.: PCT/KR2021/019586

§ 371 (c)(1),
(2) Date: Jun. 21, 2023

(87) PCT Pub. No.: WO2022/139446

PCT Pub. Date: Jun. 30, 2022

(65) Prior Publication Data

US 2024/0051919 A1 Feb. 15, 2024

(30) Foreign Application Priority Data

Dec. 22, 2020 (KR) ........................ 10-2020-0180809

(51) Int. Cl.
*C07D 207/14* (2006.01)

(52) U.S. Cl.
CPC ........ *C07D 207/14* (2013.01); *C07B 2200/13* (2013.01)

(58) Field of Classification Search
CPC ................ C07D 207/14; C07D 207/16; C07B 2200/13; A61P 3/10; A61P 15/10; A61P 29/00; A61P 3/04; A61K 31/5377
USPC ...................................................... 514/235.5
See application file for complete search history.

(56) References Cited

U.S. PATENT DOCUMENTS

| | | | |
|---|---|---|---|
| 2004/0058936 | A1 | 3/2004 | Backer et al. |
| 2007/0129346 | A1 | 6/2007 | Lee et al. |
| 2009/0298829 | A1 | 12/2009 | Choi et al. |
| 2010/0120783 | A1 | 5/2010 | Lee et al. |
| 2011/0224219 | A1 | 9/2011 | Lee et al. |
| 2011/0237795 | A1 | 9/2011 | Lee et al. |

(Continued)

FOREIGN PATENT DOCUMENTS

| | | | |
|---|---|---|---|
| CN | 102282141 | A | 12/2011 |
| EP | 4219473 | A1 | 8/2023 |

(Continued)

OTHER PUBLICATIONS

International Search Report issued for International Application No. PCT/KR2021/019586, Apr. 5, 2022, 6 pages.

(Continued)

*Primary Examiner* — Taylor V Oh
(74) *Attorney, Agent, or Firm* — Lando & Anastasi, LLP

(57) ABSTRACT

The present invention relates to a crystalline form III represented by formula 1, a method for preparing the same, and a pharmaceutical composition comprising the same. The crystalline form III represented by formula 1 of the present invention may be characterized by XRPD patterns, TG/DTA profiles, an NMR spectrum, and/or DVS profiles.

29 Claims, 3 Drawing Sheets

(56) References Cited

U.S. PATENT DOCUMENTS

| | | | | |
|---|---|---|---|---|
| 2011/0245500 | A1 | 10/2011 | Lee et al. | |
| 2013/0144077 | A1 | 6/2013 | Wu et al. | |
| 2022/0289731 | A1 | 9/2022 | Kang et al. | |
| 2023/0382895 | A1 * | 11/2023 | Ham .................... | C07D 403/06 |

FOREIGN PATENT DOCUMENTS

| | | | |
|---|---|---|---|
| EP | 4219474 | A1 | 8/2023 |
| EP | 4219475 | A4 | 3/2024 |
| KR | 10-2010-0053458 | A | 5/2010 |
| KR | 10-2014-0108222 | A | 9/2014 |
| KR | 10-1589910 | B1 | 2/2016 |
| KR | 2022-0057469 | A | 5/2022 |
| KR | 102485182 | B1 | 1/2023 |
| TW | I332501 | B | 11/2010 |
| WO | 2000/074679 | A1 | 12/2000 |
| WO | 2008-007930 | A1 | 1/2008 |
| WO | 2010-056022 | A2 | 5/2010 |
| WO | 2021-091283 | A1 | 5/2021 |
| WO | 2022/092909 | A1 | 5/2022 |
| WO | 2022/139446 | A1 | 6/2022 |

OTHER PUBLICATIONS

Caroline W. Chen et al., Synthesis and characterization of trans-4-(4-chlorophenyl) pyrrolidine-3-carboxamides of piperazinecyclohexanes as ligands for the melanocortin-4 receptor, Bioorganic & Medicinal Chemistry Letters, 2007, vol. 17, pp. 6825-6831.

Chen Chen et al., Identification and characterization of pyrrolidine diastereoisomers as potent functional agonists and antagonists of the human melanocortin-4 receptor, Bioorganic & Medicinal Chemistry Letters, 2008, vol. 18, pp. 129-136.

Joe A. Tran et al., Design and synthesis of 3-arylpyrrolidine-2-carboxamide derivatives as melanocortin-4 receptor ligands, Bioorganic & Medicinal Chemistry Letters, 2008, vol. 18, pp. 1931-1938.

Wanlong Jiang et al., Synthesis and characterization of pyrrolidine derivatives as potent agonists of the human melanocortin-4 receptor, Bioorganic & Medicinal Chemistry Letters, 2007, vol. 17, pp. 6546-6552.

Schwartz, Michael W. et al., Central nervous system control of food intake, Nature, 2000, vol. 404, pp. 661-671.

Jarl E.S. Wikberg, Melanocortin receptors: perspectives for novel drugs, European Journal of Pharmacology, 1999, 375, pp. 295-310.

Jarl E.S. Wikberg et al., New Aspects on the Melanocortins and Their Receptors, Pharmacological Research, 2000, vol. 42, No. 5, pp. 393-420.

Douglas J. MacNeil et al., "The role of melanocortins in body weight regulation: opportunities for the treatment of obesity", European Journal of Pharmacology, 2002, 450, pp. 93-109.

Stephen O'Rahilly et al., Melanocortin receptors weigh in, Nature Medicine, 2004, pp. 351-352.

Terence T. Yen et al., Obesity, diabetes, and neoplasia in yellow Avy/-mice: ectopic expression of the aqouti gene, The FASEB Journal, 1994, vol. 8, pp. 479-488.

Dongsi Lu et al., Agouti protein is an antagonist of the melanocyte-stimulating-hormone receptor, Nature, 1994, vol. 371, pp. 799-802.

John R. Shutter et al., Hypothalamic expression of ART, a novel gene related to agouti, is up-regulated in obese and diabetic mutant mice, Genes & Development, 1997, pp. 593-602.

Michael M. Ollmann et al., Antagonism of Central Melanocortin Receptors in Vitro and in Vivo by Agouti-Related Protein, Science, 1997, vol. 278, 135-138.

Ants Kask et al., Selective Antagonist for the Melanocortin 4 Receptor (HS014) Increases Food Intake in Free-Feeding Rats, Biochemical and Biophysical Research Communications, 1998, vol. 245, No. 1, pp. 90-93.

Todd E. Thiele et al., Central infusion of melanocortin agonist MTII in rats: assessment of c-Fos expression and taste aversion, the American Physiological Society, 1998, pp. R248-254.

B. Murphy et al., Centrally administered MTII affects feeding, drinking, temperature, and activity in the Sprague-Dawley rat, Journal of Applied Physiology, 2000, 89, pp. 273-282.

Donald J. Marsh et al., Response of melanocortin-4 receptor-deficient mice to anorectic and orexigenic peptides, Nature Genetics, 1999, vol. 21, pp. 119-122.

* cited by examiner

CRYSTALLINE FORM III OF MELANOCORTIN RECEPTOR AGONIST COMPOUND AND PREPARATION METHOD THEREFOR

CROSS-REFERENCE TO RELATED APPLICATIONS

This application claims the benefit of priority based on Korean Patent Application No. 10-2020-0180809, filed on 22 Dec. 2020, the entire disclosure of which is incorporated as part of the specification.

TECHNICAL FIELD

The present invention relates to a crystalline form III of a novel compound exhibiting an excellent agonistic activity for a melanocortin receptor, a method for preparing the same, and a pharmaceutical composition comprising the same.

BACKGROUND ART

Leptin protein is a hormone secreted by adipocytes, and its secretion amount increases with an increase in body fat content. It regulates functions of various neuropeptides produced from hypothalamus, thereby regulating various in vivo functions, including appetite, body fat content, and energy metabolism (Schwartz, et al., Nature 404, 661-671 (2000)). The leptin protein signal transduction for controlling appetite and body weight is made through the regulation of many factors downstream, the most representative of which are melanocortin, agouti-related peptide (AgRP), and neuropeptide Y (NPY) hormones.

When the concentration of leptin in the blood increases as a result of excess calories in vivo, the secretion of proopiomelanocortin (POMC) protein hormone from the pituitary gland increases and the production of AgRP and NPY decreases. A small peptide hormone, alpha-melanocyte-stimulating hormone (MSH), is produced from POMC neurons. The hormone is an agonist for melanocortin-4 receptors (MC4R) of second-order neurons and ultimately induces appetite decrease. Meanwhile, when the concentration of leptin decreases as a result of calorie deficiency, the expression of AgRP, an MC4R antagonist, increases, and the expression of NPY also increases, which ultimately promotes appetite. That is, according to the change of leptin, the alpha-MSH hormone and the AgRP hormone act as agonists and antagonists for MC4R and thus are involved in appetite control.

The Alpha-MSH hormone binds to three MCR subtypes in addition to MC4R to induce various physiological reactions. Five MCR subtypes have been identified so far. Among them, MC1R is expressed mainly in skin cells and is involved in regulating melanin pigmentation (skin pigmentation). MC2R is expressed mainly in the adrenal gland and is known to be involved in the production of glucocorticoid hormones. Its ligand is only adrenocorticotropic hormone (ACTH) derived from POMC. MC3R and MC4R, which are expressed mainly in the central nervous system, are involved in regulating appetite, energy metabolism, and body fat storage efficiency, and MC5R expressed in various tissues is known to regulate exocrine function (Wikberg, et al., Pharm Res 42 (5) 393-420 (2000)). In particular, activation of the MC4R receptor induce appetite decrease and energy metabolism increase and thus has an effect of efficiently reducing body weight. Therefore, it has been proven to be a major action point in the development of anti-obesity drugs (Review: Wikberg, Eur. J. Pharmacol 375, 295-310 (1999)); Wikberg, et al., Pharm Res 42 (5) 393-420 (2000); Douglas et al., Eur J Pharm 450, 93-109 (2002); O'Rahilly et al., Nature Med 10, 351-352 (2004)).

The role of MC4R in the control of appetite and body weight was primarily demonstrated through an experiment in an animal model of abnormal expression of the agouti protein (agouti mouse). In the case of the Agouti mouse, it was found that due to genetic mutation, the agouti protein was expressed at a high concentration in the central nervous system and acted as an antagonist of MC4R in the hypothalamus to cause obesity (Yen, T T et al., FASEB J. 8, 479-488 (1994); Lu D., et al. Nature 371, 799-802 (1994)). Subsequent research results showed that the agouti-related peptides (AgRP) similar to the actual agouti protein were expressed in hypothalamic nerves, and these are also known to be antagonists for MC4R and be involved in controlling appetite (Shutter, et al., Genes Dev., 11, 593-602 (1997); Ollman, et al. Science 278, 135-138 (1997)).

Intracerebral administration of alpha-MSH, which is an in vivo MC4R agonist, to animals leads to the effect of reducing appetite. When treating the animals with SHU9119 (peptide) or HS014 (peptide), which are MC4R antagonists, it was observed that appetite increased again (Kask et al., Biochem. Biophys. Res. Comm. 245, 90-93 (1998)). In addition, in animal studies using Melanotan II (MTII, Ac-Nle-c[Asp-His-DPhe-Arg-Trp-Lys]-NH2) and the similar agonist thereof, HP228, after intracerebral, intraperitoneal, or subcutaneous administration, efficiencies of inhibiting appetite, reducing body weight, increasing energy metabolism, etc. were found (Thiele T. E., et al. Am J Physiol 274 (1 Pt 2), R248-54 (1998); Lee M. D., et al. FASEB J 12, A552 (1998); Murphy B., et al. J Appl Physiol 89, 273-82 (2000)). On the contrary, administration of the representative SHU9119 to animals showed significant and sustained feed intake and weight gain, providing pharmacological evidence that MCR agonists could be anti-obesity agents. The effect of reducing appetite, which is clearly exhibited upon administration of MTII, was not observed in MC4R knock-out (KO) mice. This experimental result proves again that the appetite-reducing effect is achieved mainly through the activation of MC4R (Marsh, et al., Nat Genet 21, 119-122 (1999)).

Anorectic agents acting on the central nervous system were the main types of antiobestic drugs developed so far. Among them, most were drugs that modulate the action of neurotransmitters. Examples include noradrenalin agents (phentermine and mazindol), serotonergic agents, fluoxetine and sibutramine, and the like. However, the neurotransmitter modulators have a wide range of effects on various physiological actions in addition to appetite suppression, through numerous subtype receptors. Accordingly, the modulators lack selectivity for each subtype, and thus have a major disadvantage in that they are accompanied by various side effects when administered for a long period.

Meanwhile, melanocortin agonists are neuropeptides, not neurotransmitters. Given that in MC4R gene KO mice, all functions other than energy metabolism are normal, they have an advantage as an action point in that they can induce only weight loss through appetite suppression without affecting other physiological functions. In particular, the receptor is a G-protein coupled receptor (GPCR) that belongs to the most successful category of new drug action points developed so far. Thus, the action point greatly differs from existing action points in that it is relatively easy to secure selectivity for subtype receptors.

As an example of utilizing a melanocortin receptor as an action point, international publication nos. WO 2008/007930 and WO 2010/056022 disclose compounds as agonists of the melanocortin receptor.

In addition, the inventors of the present invention have conducted extensive studies and invented a novel compound of the following formula 1 having an excellent agonistic activity selective for a melanocortin receptor, in particular, melanocortin-4 receptor (MC4R), and a method for preparing the same (application no. KR 10-2019-0141649 (filed on 7 Nov. 2019)):

[Formula 1]

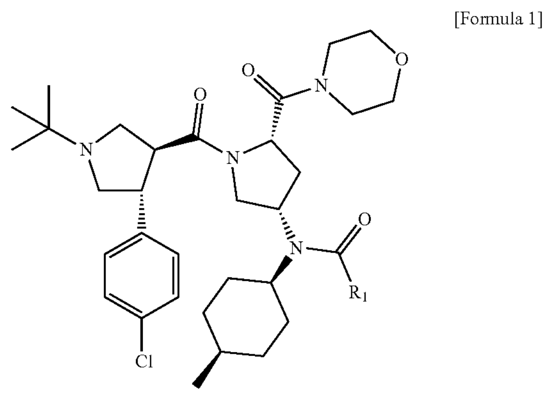

($R_1$ is $C_2$-$C_5$ alkyl.)

Meanwhile, the crystal structure of a pharmaceutically active ingredient often affects the chemical stability of the drug. Different crystallization conditions and storage conditions can lead to changes in the crystal structure of the compound, and sometimes the accompanying production of other forms of the crystalline form. In general, an amorphous drug product does not have a regular crystal structure, and often has other defects such as poor product stability, smaller particle size, difficult filtration, easy agglomeration, and poor flowability. Thus, it is necessary to improve various physical properties of the product. As such, it is necessary to study crystal structures having high purity and good chemical stability for a single compound.

PRIOR ART DOCUMENTS

Patent Documents (Patent Document 1) International Patent Application Publication No. WO 2008/007930

(Patent Document 2) International Patent Application Publication No. WO 2010/056022

DISCLOSURE OF THE INVENTION

Technical Problem

An objective of the present invention provides a stable crystalline form of a novel compound having an excellent agonistic activity, which is selective for a melanocortin receptor, in particular, melanocortin-4 receptor (MC4R), and a method for preparing the same.

Another objective of the present invention provides a pharmaceutical composition comprising the stable crystalline form of the novel compound.

Technical Solution

To achieve the above objectives,

According to an aspect of the present invention, there is provided a crystalline form III of a compound of the following formula 1, a pharmaceutically acceptable salt, or a solvate thereof, wherein the X-ray powder diffraction (XRPD) pattern has 3 or more characteristic peaks selected from among peaks with the following diffraction angles (2θ values) of: 6.238±0.2°, 8.257±0.2°, 8.828±0.2°, 14.637±0.2°, 16.618±0.2°, 17.465±0.2°, 18.859±0.2°, 19.061±0.2°, 19.333±0.2°, 20.642±0.2°, 22.679±0.2°, and 25.985±0.2°,

[Formula 1]

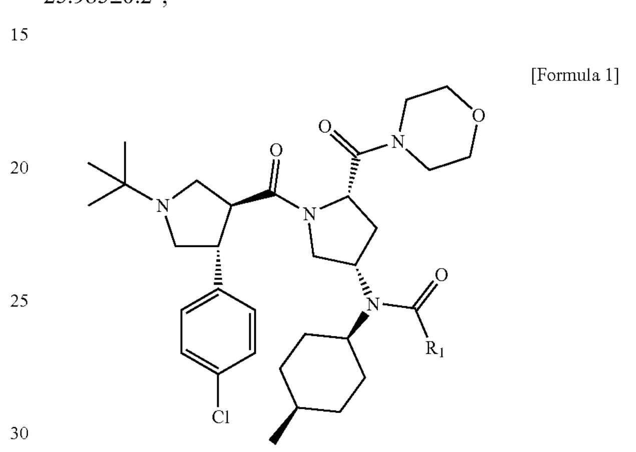

In formula 1, $R_1$ is $C_2$-$C_5$ alkyl.

Since the compound of formula 1 can have an asymmetric carbon center and an asymmetric axis or an asymmetric plane, it can exist as cis or trans isomers, R or S isomers, racemates, diastereomer mixtures, and individual diastereomers, all of which are within the scope of the compound of formula 1.

In the present specification, unless otherwise specified for convenience, the compound of formula 1 is used to include all of the compound of formula 1, a pharmaceutically acceptable salt, an isomer, and a solvate thereof.

In one embodiment, according to the present invention, in formula 1, $R_1$ is $C_2$ to $C_5$ alkyl. In another embodiment, according to the present invention, in formula 1, $R_1$ is a straight-chain or branched $C_2$ to $C_5$ alkyl, for example, ethyl, n-propyl, iso-propyl, n-butyl, iso-butyl, sec-butyl, or tert-butyl.

In another embodiment, according to the present invention, in formula 1, $R_1$ is $C_2$ or $C_4$ alkyl. In another embodiment, according to the present invention, in formula 1, $R_1$ is a straight-chain or branched $C_2$ to $C_4$ alkyl, for example, ethyl, n-propyl, iso-propyl, n-butyl, sec-butyl, or tert-butyl. Specifically, $R_1$ may be iso-propyl.

In one embodiment, according to the present invention, the pharmaceutically acceptable salt includes, but is not limited to, acid-addition salts which are formed from inorganic acids, such as hydrochloric acid, sulfuric acid, nitric acid, phosphoric acid, hydrobromic acid, and hydroiodic acid; organic carbonic acids, such as tartaric acid, formic acid, citric acid, acetic acid, trichloroacetic acid, trifluoroacetic acid, gluconic acid, benzoic acid, lactic acid, fumaric acid, and maleic acid; or sulfonic acids, such as methanesulfonic acid, benzenesulfonic acid, toluenesulfonic acid, or naphthalene-sulfonic acid.

In one embodiment, according to the present invention, the solvate may include a hydrate; and a solvate with an organic solvent, such as methanol, ethanol, 2-propanol, 1,2-propanediol, 1,3-propanediol, n-butanol, 1,4-butanediol, tert-butanol, acetic acid, acetone, butyl acetate, methyl acetate, ethyl acetate, propyl acetate, t-butyl acetate, isobutyl acetate, methylethylketone, 2-pentanone, tetrahydrofuran, acetonitrile, formamide, N,N-dimethylformamide, N-methyl-2-pyrrolidone, chloroform, toluene, and mixtures thereof.

In one embodiment, according to the present invention, the crystalline form III may be a crystalline form of a solvate of the compound of formula 1 with an amide-based solvent.

In another embodiment, according to the present invention, the crystalline form III may be a crystalline form of a formamide solvate of formula 1.

In one embodiment, according to the present invention, the crystalline form III may have 3 or more, 5 or more, 7 or more, 9 or more, 10 or more, or 11 or more characteristic peaks selected from among peaks with 2θ values of: 6.238±0.2°, 8.257±0.2°, 8.828±0.2°, 14.637±0.2°, 16.618±0.2°, 17.465±0.2°, 18.859±0.2°, 19.061±0.2°, 19.333±0.2°, 20.642±0.2°, 22.679±0.2°, and 25.985±0.2° in the X-ray powder diffraction pattern.

In one embodiment, according to the present invention, the crystalline form III may have characteristic peaks with 2θ values of: 6.238±0.2°, 8.257±0.2°, 8.828±0.2°, 14.637±0.2°, 16.618±0.2°, 17.465±0.2°, 18.859±0.2°, 19.061±0.2°, 19.333±0.2°, 20.642±0.2°, 22.679±0.2°, and 25.985±0.2° in the X-ray powder diffraction pattern.

The crystalline form III, according to the present invention, may be a crystalline form of a solvate of the compound of formula 1, and thus, a halo due to a residual solvent may be observed during the XRPD measurement. For example, the XRPD peak observed at a 2θ angle of 20 to 30° may be a halo due to a residual solvent, such as formamide.

In one embodiment, according to the present invention, the crystalline form III may have the X-ray powder diffraction (XRPD) pattern shown in FIG. 1.

The crystalline form III, according to the present invention, may have two endothermic peaks at 80 to 130° C. and 200 to 260° C. in a differential scanning calorimetry (DSC) profile.

In particular, the crystalline form III, according to the present invention, may contain an endothermic peak (200 to 260° C.) due to a solvent, for example, formamide in a differential scanning calorimetry (DSC) profile.

In addition, the crystalline form III, according to the present invention, may have a weight loss of 10% or less, for example, 5% or less, 4% or less, 3% or less, 2% or less, 1.5% or less, or 1.2% in the range where the endothermic peak at 80 to 130° C. appears in the DSC profile.

In addition, the crystalline form III, according to the present invention, may have a weight loss of 20 to 40%, for example, 25% to 30%, or 27.9% in the range where the endothermic peak at 200 to 260° C. appears in the DSC profile.

In one embodiment, according to the present invention, the crystalline form III may have the TG/DTA profile shown in FIG. 2. A peak due to a solvent, for example, formamide, may be contained in the NMR analysis result for the crystalline form III.

In one embodiment, according to the present invention, the crystalline form III may have the NMR result shown in FIG. 3.

In the present specification,

X-ray powder diffraction (XRPD) analysis shows the results obtained using PANalytical X' Pert Pro MPD system (Malvern Panalytical Ltd.).

Thermogravimetric analysis (TG/DTA) shows the results obtained using TGA/DSC 1 (Mettler-Toledo AG).

The nuclear magnetic resonance (NMR) result shows the result obtained using Bruker 500 MHz.

The crystalline form III may have higher purity than a crude compound of formula 1, an amorphous compound of formula 1, or other crystalline forms of the compound of formula 1, and may be physically and chemically more stable.

In addition, the agonistic ability for the melanocortin-4 receptor and preventive or therapeutic effects on diseases, such as obesity, diabetes, inflammation, erectile dysfunction, or the like, of the crystalline form III of the compound of formula 1, can be more excellent than those of known melanocortin-4 receptor agonists. However, the effects of the present invention are not limited thereto.

In another aspect, the present invention provides a method for preparing the crystalline form III, comprising the steps of: preparing a mixed solution by dissolving the compound of formula 1 in a crystallization solvent; and obtaining crystals from the mixed solution.

First, the compound represented by formula 1 is dissolved in a crystallization solvent.

The compound of formula 1 for preparing the crystalline form III may be a compound of formula 1, a salt thereof, an isomer thereof, or a solvate thereof.

The compound of formula 1 may be obtained by the preparation method described in the specification of application no. KR 10-2019-0141649 (filed on 7 Nov. 2019).

The crystallization solvent may be used without particular limitation as long as it is a suitable solvent for crystallization of compounds. In one embodiment, the crystalline solvent includes a polar organic solvent.

The polar organic solvent may include, but is not limited to, an amide-based solvent.

Examples of the amide-based solvent include, but are not limited to, formamide, N,N-dimethylformamide, N-methyl-2-pyrrolidone, or mixtures thereof.

In one embodiment, according to the present invention, the polar organic solvent may include formamide.

In one embodiment, according to the present invention, the step of obtaining crystals may be performed by anti-solvent crystallization (precipitation with anti-solvent).

In the anti-solvent crystallization, the crystallization solvent for dissolving the compound of formula 1 may be the above-described polar organic solvent, for example, formamide, and an anti-solvent may be at least one of a non-polar organic solvent and water. The non-polar organic solvent may be used without particular limitation as long as it is an organic solvent having non-polar properties, but, for example, hexane, heptane, cyclohexane, carbon tetrachloride, benzene, chloroform, and the like, may be used.

In one embodiment, according to the present invention, the crystalline form III may be obtained by dissolving the compound of formula 1 in formamide and then adding heptane, as the anti-solvent, dropwise.

In another embodiment, according to the present invention, the step of obtaining crystals may be performed by slurry method (slurry experiment).

The slurry method may be carried out by dissolving the compound of formula 1 in a sufficient amount of a solvent at a desired temperature until undissolved solids remain, sealing, stirring for a period of time while maintaining the temperature, filtering, and drying. However, the slurry method is not limited thereto.

In the slurry method, the crystallization solvent for dissolving the compound of formula 1 may be, but is not limited to, the above-described polar organic solvent, for example, formamide.

In one embodiment, according to the present invention, the crystalline form III may be obtained by adding the compound of formula 1 to a sufficient amount of the crystallization solvent at a constant temperature of 0 to 80° C. until solids remain, sealing so that the temperature is maintained, and stirring for 1 to 60 days.

In the slurry method, the constant temperature may be, but is not limited to, for example, 0° C. to 80° C., 5° C. to 60° C., 5° C. to 50° C., 5° C. to 20° C., 20° C. to 50° C., 15° C. to 60° C., 5° C., 20° C., or 50° C.

In the slurry method, the period for which the compound dissolved in the crystallization solvent is maintained may be, but is not limited to, for example, 1 to 60 days, 1 to 30 days, 1 to 15 days, 1 to 10 days, 5 to 7 days, or 6 days.

The crystalline form III as obtained above may have higher purity than a crude compound of formula 1, an amorphous compound of formula 1, or any other crystalline forms of formula 1, and may be physically and chemically more stable. However, the effects of the present invention are not limited thereto.

In another aspect, the present invention provides a pharmaceutical composition comprising: (i) the crystalline form III; and (ii) a pharmaceutically acceptable carrier.

The crystalline form III, according to the present invention exhibits excellent agonistic actions on melanocortin receptors, in particular, melanocortin-4 receptors (MC4R). Thus, the present invention can provide a pharmaceutical composition for agonizing melanocortin receptors, the composition containing the above-described crystalline form III as an active ingredient. Specifically, the pharmaceutical composition may be a composition for agonizing the function of the melanocortin-4 receptor.

In addition, since the pharmaceutical composition can exhibit excellent effects of preventing or treating obesity, diabetes, inflammation, and erectile dysfunction, it may be a composition for preventing or treating obesity, diabetes, inflammation, or erectile dysfunction. However, the use of the present invention is not limited the diseases.

As used herein, "carrier" refers to a compound that facilitates the introduction of compounds into a cell or tissue.

When the crystalline form III of the present invention is administered for clinical purposes, the total daily dose to be administered to a host in a single dose or in divided doses may be preferably in the range of 0.01 to 10 mg/kg body weight. However, the specific dose level for an individual patient may vary depending on the specific compound to be used, the patient's weight, sex, health status, diet, administration time of the drug, administration method, excretion rate, drug combination, the severity of the disease, or the like.

The crystalline form III of the present invention may be administered by any route as desired. For example, the amorphous compound of the present invention may be administered by injection or orally.

The pharmaceutical composition of the present invention may be in various oral dosage forms, such as tablets, pills, powders, capsules, granules, syrups, or emulsions, or parenteral dosage forms, such as injection preparations for intramuscular, intravenous, or subcutaneous administration.

Preparations for injection may be prepared according to known techniques using suitable dispersing agents, wetting agents, suspending agents, or excipients.

Excipients that can be used in the pharmaceutical preparation of the present invention include, but are not limited to, sweeteners, binders, solubilizers, solubilizing agents, wetting agents, emulsifiers, isotonic agents, adsorbents, disintegrants, antioxidants, preservatives, lubricants, fillers, fragrances, etc. For example, as excipients, lactose, dextrose, sucrose, mannitol, sorbitol, cellulose, glycine, silica, magnesium aluminum silicate, starch, gelatin, gum tragacanth, arginic acid, sodium alginate, methylcellulose, sodium carboxymethyl cellulose, water, ethanol, polyethylene glycol, polyvinyl pyrrolidone, sodium chloride, calcium chloride, orange essence, strawberry essence, vanilla flavor, etc. may be used.

When the pharmaceutical composition of the present invention is in an oral dosage form, examples of the carrier to be used may include, but are not limited to, cellulose, calcium silicate, corn starch, lactose, sucrose, dextrose, calcium phosphate, stearic acid, magnesium stearate, calcium stearate, gelatin, talc, etc.

When the pharmaceutical composition of the present invention is in an injectable preparation form, examples of the carrier may include, but are not limited to, water, saline, aqueous glucose solution, an aqueous sugar-like solution, alcohols, glycol, ethers, oils, fatty acids, fatty acid esters, glycerides, etc.

In another aspect, there is provided a crystalline form III as described above for use in agonizing the functions of melanocortin receptors, in particular, melanocortin-4 receptors (MC4R).

In one embodiment, there is provided a crystalline form III as described above for use in treating or preventing obesity, diabetes, inflammation, or erectile dysfunction.

In another aspect, there is provided a method for agonizing the function of melanocortin receptors, in particular, melanocortin-4 receptors (MC4R), the method comprising a step for administering to a subject the above-described crystalline form III.

In another aspect, there is provided a method for treating obesity, diabetes, inflammation, or erectile dysfunction, the method comprising a step for administering to a subject the above-described crystalline form III.

Advantageous Effects

The crystalline form III, according to the present invention, exhibits excellent agonistic action on melanocortin receptors, in particular, melanocortin-4 receptors (MC4R), and thus can be usefully used for preventing or treating obesity, diabetes, inflammation, and erectile dysfunction.

The crystalline form III, according to the present invention, exhibits an on-target effect on melanocortin-4 receptors, thereby exhibiting weight loss and diet reduction effects, without affecting anxiety and depression. In addition, it can be administered without any safety issues, such as side effects of human ether-a-go-go related gene (hERG) inhibition or mutagenesis.

In addition, the crystalline form III, according to the present invention, has purity, yield, physical and chemical stability, which are more excellent than the crude compound of formula 1, the amorphous compound of formula 1, or any other crystalline forms of formula 1.

Specifically, the crystalline form III may have superior solubility, storage stability, and production stability to the compound of formula 1, the amorphous compound of formula 1, or any other crystalline forms of formula 1.

MODE FOR CARRYING OUT THE INVENTION

Figure 1:
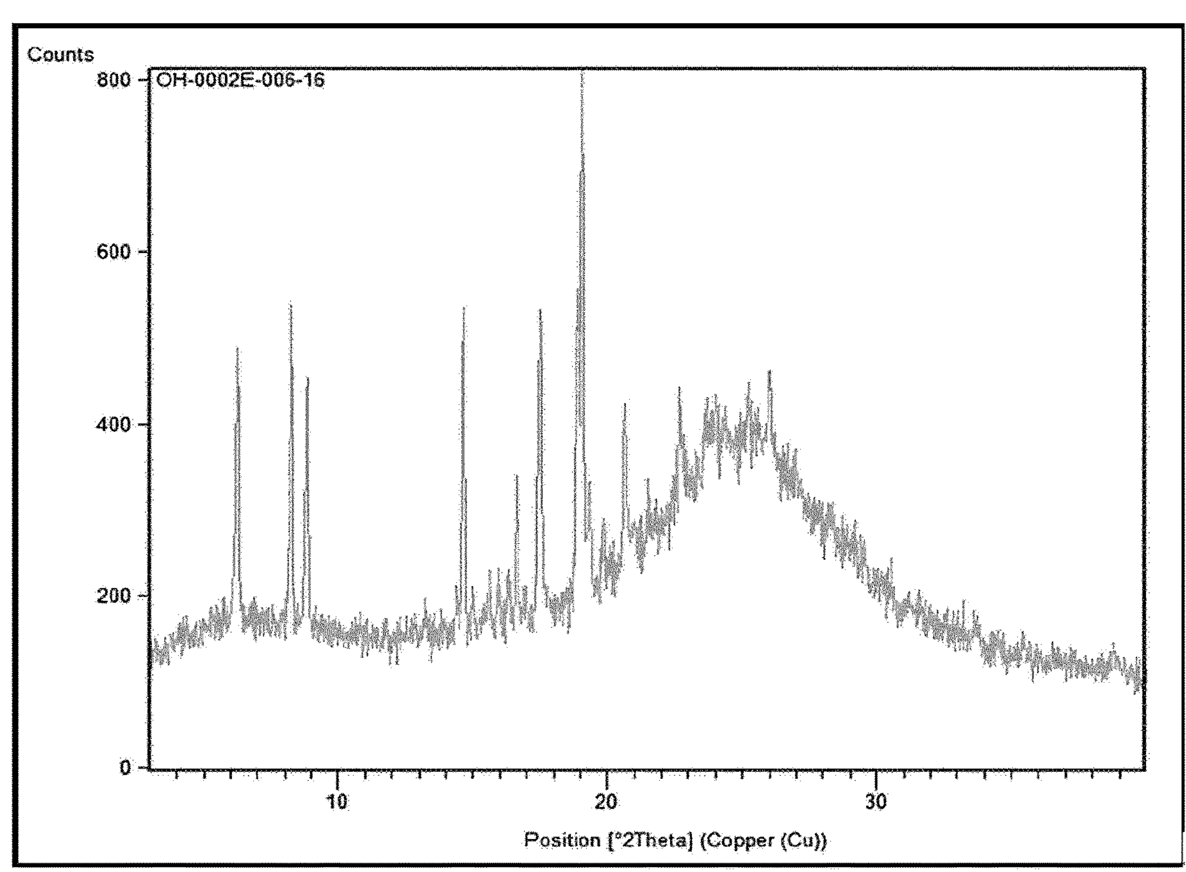
FIG. 1 is the graph of the XRPD result of Example 1.

Hereinafter, the present invention will be described in more detail through Preparation Examples and Examples. However, these Examples are merely illustrative of the present invention, and the scope of the present invention is not limited thereto.

Preparation Example 1: Preparation of methyl (2S,4S)-4-(N-((1s,4R)-4-methylcyclohexyl)isobutyramido)pyrrolidine-2-carboxylate hydrochloride

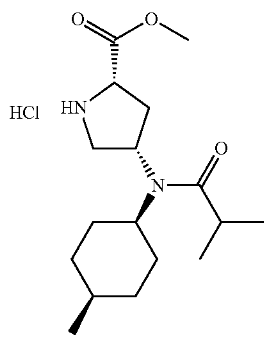 [SMILES: Cl ; COC(=O)[C@@H]1C[C@H](N(C(=O)C(C)C)[C@H]2CC[C@@H](C)CC2)CN1]

The title compound was obtained through the following steps A, B, C, D, and E.

Step A: Preparation of 1-(tert-butyl) 2-methyl (2S,4S)-4-azidopyrrolidine-1,2-dicarboxylate 1-(tert-butyl) 2-methyl (2S,4R)-4-((methylsulfonyl)oxy) pyrrolidine-1,2-dicarboxylate (48.5 g, 150 mmol) was dissolved in N,N'-dimethylformamide (250 ml) under nitrogen, and sodium azide (19.5 g, 300 ml) was added. After stirring at 80° C. for 16 hours, the reaction solvent was concentrated under reduced pressure, water was added, and extraction was performed twice with ethyl acetate. The organic layer was washed with an aqueous sodium chloride solution and water, dried over anhydrous magnesium sulfate, and filtered. The filtrate was concentrated under reduced pressure to obtain crude 1-(tert-butyl) 2-methyl (2S,4S)-4-azidopyrrolidine-1,2-dicarboxylate (39.59 g, 98%), which was used in the next step without purification.

MS [M+H]=271 (M+1)

$^1$H NMR (400 MHz, CD3OD) δ 4.43-4.37 (m, 1H), 4.35-4.27 (br, 1H), 3.77 (s, 1.8H), 3.76 (s, 1.2H), 3.73-3.66 (m, 1H), 3.44-3.38 (m, 1H), 2.63-2.49 (m, 1H), 2.19-2.11 (m, 1H), 1.50 (s, 4.5H), 1.44 (s, 4.5H)

Step B: Preparation of 1-(tert-butyl) 2-methyl (2S,4S)-4-aminopyrrolidine-1,2-dicarboxylate 1-(tert-butyl) 2-methyl (2S,4S)-4-azidopyrrolidine-1,2-dicarboxylate (24.59 g, 91.0 mmol) obtained in step A above was dissolved in tetrahydrofuran (180 ml), and 1 M trimethylphosphine tetrahydro solution (109.2 ml, 109.2 mmol) was slowly added at 0° C. After stirring at the same temperature for 1 hour, the mixture was stirred at room temperature for 3 hours. After the reaction solvent was concentrated under reduced pressure, dichloromethane (100 ml) and water (150 ml) were added, and the mixture was stirred for about 30 minutes. The layers were separated and were extracted once more with dichloromethane, and the organic layer was dried over anhydrous magnesium sulfate and was filtered. The filtrate was concentrated under reduced pressure to obtain crude 1-(tert-butyl) 2-methyl (2S,4S)-4-aminopyrrolidine-1,2-dicarboxylate (20.62 g, 93%), which was used in the next step without purification.

MS [M+H]=245 (M+1)

$^{1H}$ NMR (400 MHz, CD3OD) δ 4.27 (m, 1H), 3.77 (s, 1.8H), 3.76 (s, 1.2H), 3.75-3.67 (m, 1H), 3.50-3.42 (m, 1H), 3.22-3.17 (m, 1H), 2.58-2.47 (m, 1H), 1.82-1.71 (m, 1H), 1.48 (s, 4.5H), 1.42 (s, 4.5H)

Step C: Preparation of 1-(tert-butyl) 2-methyl (2S,4S)-4-(((1s,4R)-4-methylcyclohexyl)amino)pyrrolidine-1,2-dicarboxylate 1-(tert-butyl) 2-methyl (2S,4S)-4-aminopyrrolidine-1,2-dicarboxylate (20.62 g, 84.4 mmol) obtained in step B above was dissolved in dichloroethane (150 ml), and 4-methylcyclohexanone (9.5 ml, 101.3 mmol) was added. Sodium triacetoxyborohydride (26.8 g, 126.6 mmol) was added at 0° C., and the mixture was stirred at room temperature for 16 hours. The reaction solvent was concentrated under reduced pressure, water was added, and extraction was performed twice with ethyl acetate. The organic layer was washed with an aqueous sodium chloride solution, dried over anhydrous magnesium sulfate, and filtered. The filtrate was concentrated under reduced pressure and purified by column chromatography to obtain 1-(tert-butyl) 2-methyl (2S,4S)-4-(((1s,4R)-4-methylcyclohexyl)amino)pyrrolidine-1,2-dicarboxylate (22.9 g, 80%).

MS [M+H]=341 (M+1)

$^{1H}$ NMR (400 MHz, CD3OD) δ 4.26 (m, 1H), 3.76 (s, 1.8H), 3.75 (s, 1.2H), 3.78-3.71 (m, 1H), 3.49-3.40 (m, 1H), 3.22-3.16 (m, 1H), 2.69-2.60 (br, 1H), 2.58-2.46 (m, 1H), 1.87-1.77 (m, 1H), 1.73-1.63 (m, 1H), 1.62-1.35 (m, 8H), 1.48 (s, 4.5H), 1.42 (s, 4.5H), 0.96 (d, 3H)

Step D: Preparation of 1-(tert-butyl) 2-methyl (2S,4S)-4-(N-((1s,4R)-4-methylcyclohexyl)isobutyramido)pyrrolidine-1,2-dicarboxylate 1-(tert-butyl) 2-methyl (2S,4S)-4-(((1s,4R)-4-methylcyclohexyl)amino)pyrrolidine-1,2-dicarboxylate obtained in step C above (37.29 g, 109.5 mmol) was dissolved in dichloromethane (500 ml), triethyl amine (61.1 ml, 438.1 mmol) was added, and then isobutyryl chloride (11.7 ml, 219 mmol) was slowly added at 0° C. After stirring at room temperature for 16 hours, the reaction solvent was concentrated under reduced pressure, an aqueous sodium hydrogen carbonate solution was added, and extraction was performed twice with ethyl acetate. The organic layer was washed with an aqueous sodium chloride solution and water, dried over anhydrous magnesium sulfate, and filtered. The filtrate was concentrated under reduced pressure, and purified by column chromatography to obtain 1-(tert-butyl) 2-methyl (2S,4S)-4-(N-((1s,4R)-4-methylcyclohexyl)isobutyramido)pyrrolidine-1,2-dicarboxylate (38.79 g, 86%).

MS [M+H]=411 (M+1)

$^{1H}$ NMR (400 MHz, CD3OD) δ 4.27 (m, 1H), 3.76 (s, 1.8H), 3.75 (s, 1.2H), 3.78-3.72 (m, 1H), 3.50-3.41 (m, 1H), 3.33-3.14 (m, 1H), 2.69-2.60 (m, 2H), 2.57-2.43 (m, 1H), 1.87-1.79 (m, 1H), 1.70-1.61 (m, 1H), 1.60-1.32 (m, 8H), 1.47 (s, 4.5H), 1.41 (s, 4.5H), 1.10 (dd, 6H), 0.99 (d, 3H)

Step E: Preparation of methyl (2S,4S)-4-(N-((1s,4R)-4-methylcyclohexyl)isobutyramido)pyrrolidine-2-carboxylate hydrochloride 1-(tert-butyl) 2-methyl (2S,4S)-4-(N-((1s,4R)-4-methylcyclohexyl)isobutyramido)pyrrolidine-1,2-dicarboxylate (34.0 g, 82.8 mmol) obtained in step D above was dissolved in dichloromethane (200 ml), and a solution of 4 N hydrochloric acid in 1,4-dioxane solution (82.8 ml, 331.3 mmol) was added at 0° C. After stirring at room temperature for 6 hours, the reaction solvent was concentrated under reduced pressure to obtain crude (28.7 g, 99%), which was used in the next step without purification.

MS[M+H]=311 (M+1)

Preparation Example 2: Preparation of (3S,4R)-1-(tert-butyl)-4-(4-chlorophenyl)pyrrolidine-3-carboxylic acid

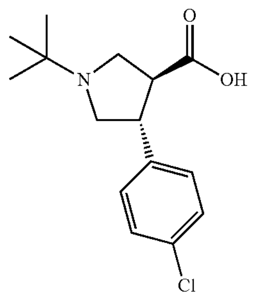 [SMILES: CC(C)(C)N1C[C@@H](C(=O)O)[C@H](c2ccc(Cl)cc2)C1]

The title compound was obtained according to the method described in international patent publication no. WO 2004/092126.

MS[M+H]=282 (M+1)

$^{1}$H NMR (400 MHz, CD3OD) δ 7.43-7.33 (m, 4H), 3.90-3.69 (m, 3H), 3.59 (dd, J=11.2, 10.0 Hz, 1H), 3.29 (dd, J=11.2, 11.2 Hz, 1H), 3.18-3.09 (m, 1H), 1.44 (s, 9H)

Preparation Example 3: Preparation of N-((3S,5S)-1-((3S,4R)-1-(tert-butyl)-4-(4-chlorophenyl)pyrrolidine-3-carbonyl)-5-(morpholine-4-carbonyl)pyrrolidin-3-yl)-N-((1s,4R)-4-methylcyclohexyl)isobutyramide (MC70)

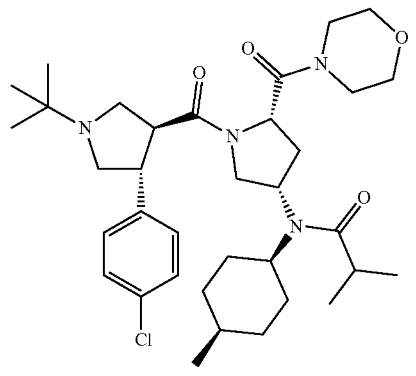 [SMILES: CC(C)C(=O)N([C@H]1C[C@@H](C(=O)N2CCOCC2)N(C(=O)[C@@H]2CN(C(C)(C)C)C[C@H]2c2ccc(Cl)cc2)C1)[C@H]1CC[C@@H](C)CC1]

The title compound was obtained through the following steps A, B, and C.

Step A: Preparation of methyl (2S,4S)-1-((3S,4R)-1-(tert-butyl)-4-(4-chlorophenyl)pyrrolidine-3-carbonyl)-4-(N-((1s,4R)-4-methylcyclohexyl)isobutyramido)pyrrolidine-2-carboxylate Methyl (2S,4S)-4-(N-((1s,4R)-4-methylcyclohexyl)isobutyramido)pyrrolidine-2-carboxylate hydrochloride (28.7 g, 82.73 mmol) obtained in Preparation Example 1, (3S,4R)-1-(tert-butyl)-4-(4-chlorophenyl)pyrrolidine-3-carboxylic acid (24.5 g, 86.87 mmol) obtained in Preparation Example 2, 1-(3-dimethylaminopropyl)-3-ethylcarbodiimide hydrochloride (22.2 g, 115.83 mmol), and 1-hydroxybenzotriazole hydrate (15.7 g, 115.83 mmol) were dissolved in N,N'-dimethylformamide (400 ml), and N,N'-diisopropylethylamine (72.0 ml, 413.66 mmol) was added slowly. After stirring at room temperature for 16 hours, the reaction solvent was concentrated under reduced pressure, 0.5 N sodium hydroxide aqueous solution was added, and extraction was performed twice with ethyl acetate. The organic layer was washed twice with sodium chloride aqueous solution and water, dried over anhydrous magnesium sulfate, and filtered. The filtrate was concentrated under reduced pressure and purified by column chromatography to obtain methyl (2S,4S)-1-((3S,4R)-1-(tert-butyl)-4-(4-chlorophenyl)pyrrolidine-3-carbonyl)-4-(N-((1s,4R)-4-methylcyclohexyl)isobutyramido)pyrrolidine-2-carboxylate (41.19 g, 87%).

MS [M+H]=575 (M+1)

Step B: Preparation of (2S,4S)-1-((3S,4R)-1-(tert-butyl)-4-(4-chlorophenyl)pyrrolidine-3-carbonyl)-4-(N-((1s,4R)-4-methylcyclohexyl)isobutyramido)pyrrolidine-2-carboxylic acid Methyl (2S,4S)-1-((3S,4R)-1-(tert-butyl)-4-(4-chlorophenyl)pyrrolidine-3-carbonyl)-4-(N-((1s,4R)-4-methylcyclohexyl)isobutyramido)pyrrolidine-2-carboxylate (39.4 g, 68.62 mmol) obtained in step A above was dissolved in methanol (450 ml), and then, 6 N sodium hydroxide aqueous solution (57.2 ml, 343.09 mmol) was added. After stirring at room temperature for 16 hours, and adjusting the pH to about 5 with 6 N aqueous hydrochloric acid solution, the reaction solution was concentrated under reduced pressure. After dissolving the concentrate in dichloromethane, the insoluble solid was filtered through a paper filter. The filtrate was concentrated under reduced pressure to obtain the crude title compound (38.4 g, 99%), which was used in the next step without purification.

MS [M+H]=561 (M+1)

Step C: Preparation of N-((3S,5S)-1-((3S,4R)-1-(tert-butyl)-4-(4-chlorophenyl)pyrrolidine-3-carbonyl)-5-(morpholine-4-carbonyl)pyrrolidin-3-yl)-N-((1s,4R)-4-methylcyclohexyl)isobutyramide (2S,4S)-1-((3S,4R)-1-(tert-butyl)-4-(4-chlorophenyl)pyrrolidine-3-carbonyl)-4-(N-((1s,4R)-4-methylcyclohexyl) isobutyramido)pyrrolidine-2-carboxylic acid (38.4 g, 68.60 mmol) obtained in step B above, 1-(3-dimethylaminopropyl)-3-ethylcarbodiimide hydrochloride (18.4 g, 96.04 mmol), and 1-hydroxybenzotriazole hydrate (13.0 g, 96.04 mmol) were dissolved in N,N'-dimethylformamide (200 ml), and then morpholine (5.9 ml, 68.80 mmol) and N,N'-diisopropylethylamine (59.7 ml, 343.02 mmol) were sequentially and slowly added. After stirring at room temperature for 16 hours, the reaction solution was concentrated under reduced pressure, 0.5 N sodium hydroxide aqueous solution was added, and extraction was performed twice with ethyl acetate. The organic layer was washed twice with sodium chloride aqueous solution and water, dried over anhydrous magnesium sulfate, and filtered. The filtrate was concentrated under reduced pressure and purified by column chromatography to obtain N-((3S,5S)-1-((3S,4R)-1-(tert-butyl)-4-(4-chlorophenyl)pyrrolidine-3-carbonyl)-5-(morpholine-4-carbonyl)pyrrolidin-3-yl)-N-((1s,4R)-4-methylcyclohexyl)isobutyramide (37.05 g, 86% m, MC70).

MS [M+H]=630 (M+1)

[Examples] Preparation of Crystalline form III of N-((3S,5S)-1-((3S,4R)-1-(tert-butyl)-4-(4-chlorophenyl)pyrrolidine-3-carbonyl)-5-(morpholine-4-carbonyl)pyrrolidin-3-yl)-N-((1s, 4R)-4-methylcyclohexyl)isobutyramide

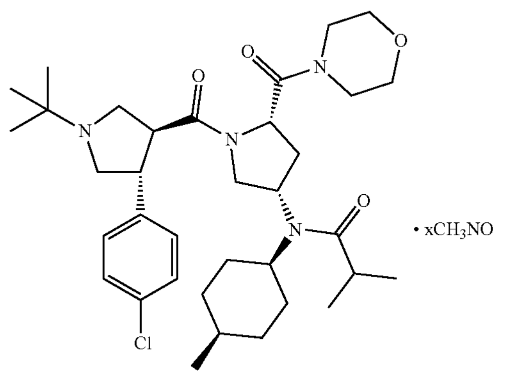 [SMILES: CC(C)C(=O)N([C@H]1C[C@@H](C(=O)N2CCOCC2)N(C(=O)[C@@H]2CN(C(C)(C)C)C[C@H]2c2ccc(Cl)cc2)C1)[C@H]1CC[C@@H](C)CC1]

Example 1: Preparation by Anti-Solvent Method 25 mg of the compound (MC70) prepared in Preparation Example 3 was dissolved in formamide. Then, heptane with 19 times the volume of formamide was introduced as an anti-solvent at room temperature. Then, the mixture was stored at 4° C. for 7 to 14 days, filtered, and dried to obtain the title compound (the crystalline form III of MC70).

Example 2: Preparation by Slurry Method 25 mg of the compound (MC70) prepared in Preparation Example 3 was added to a sufficient amount of formamide until undissolved solids remained at the desired temperature (5° C.) After sealing the test tube, the mixture was stirred for 6 days while maintaining the desired temperature (5° C.). Then, the mixture was filtered and dried to obtain the title compound (the crystalline form III of MC70).

Example 3: Preparation by Slurry Method

The title compound (the crystalline form III of MC70) was obtained in the same manner as in Example 2, except that the desired temperature was set to 20° C.

Example 4: Preparation by Slurry Method

The title compound (the crystalline form III of MC70) was obtained in the same manner as in Example 2, except that the desired temperature was set to 50° C.

The XRPD, TG/DTA, NMR, and DVS analyses were performed on the compounds obtained in Examples 1 to 4 in the following manner. The analysis results showed that the compounds obtained in Examples 1 to 4 had the same crystalline form.

Figure 2:
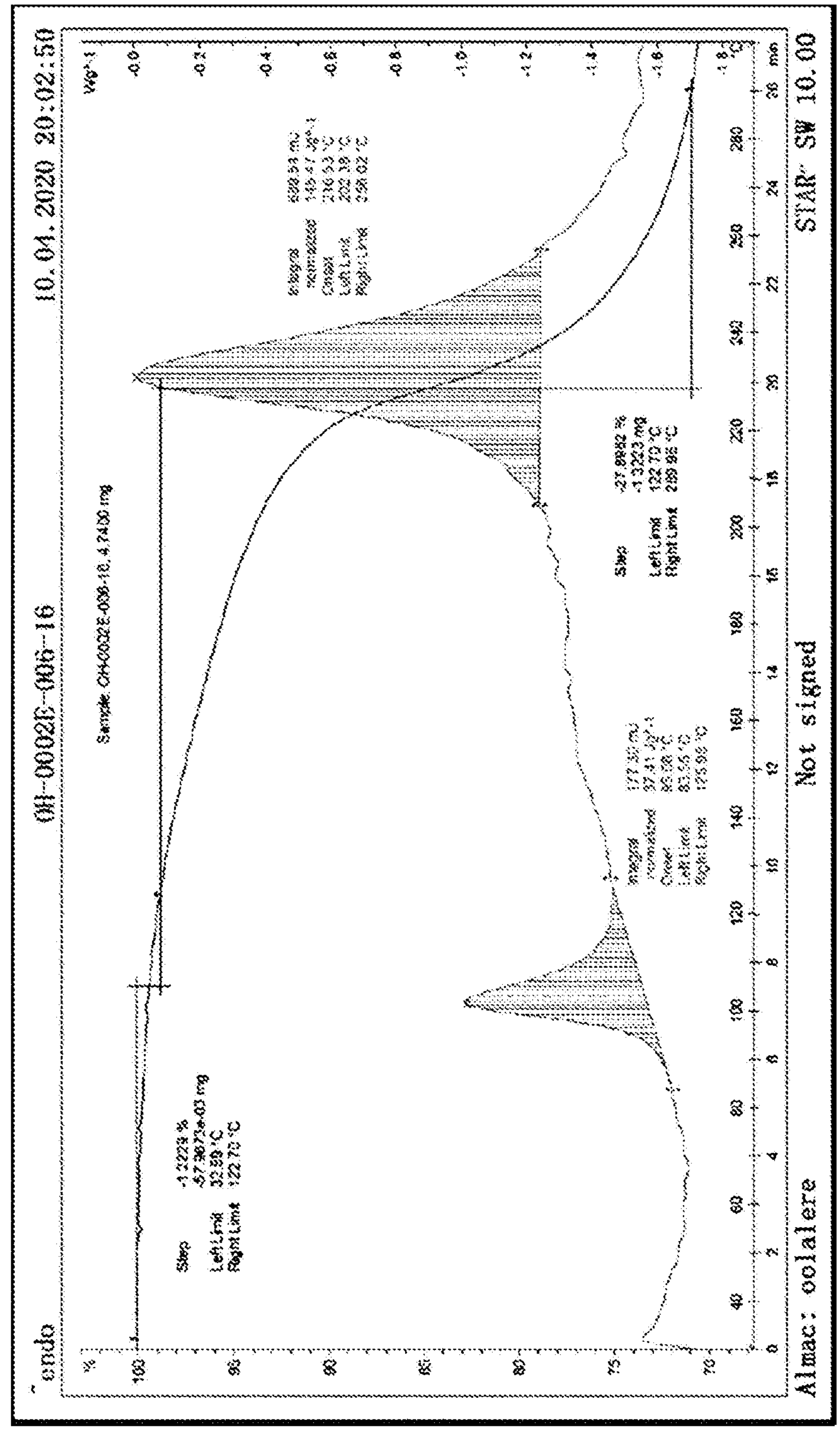
FIG. 2 is the graph of the TG/DTA result of Example 1.
Figure 3:
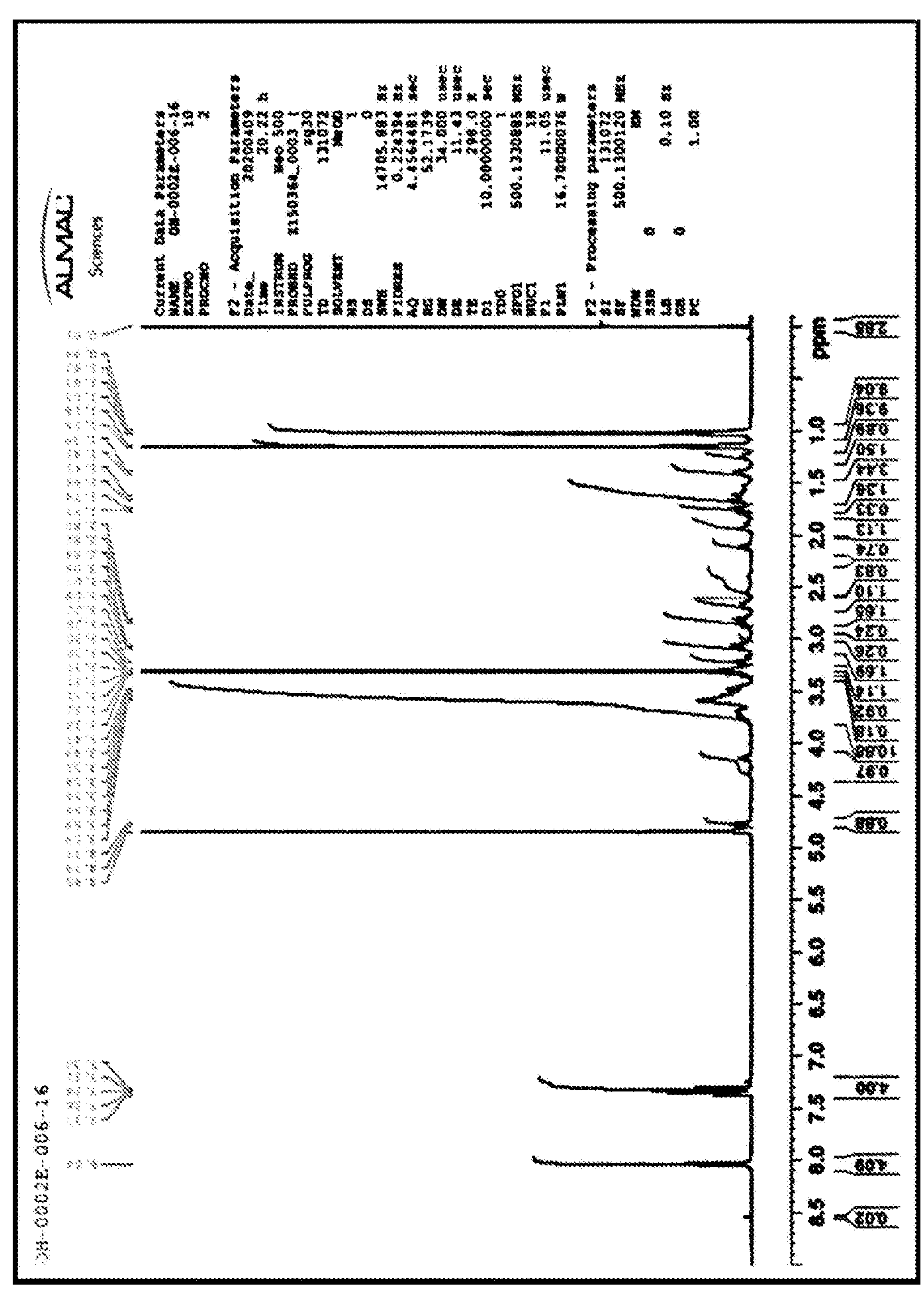
FIG. 3 is the graph of the NMR result of Example 1.

The resulting graphs of the XRPD (FIG. 1), TG/DTA (FIG. 2), and NMR (FIG. 3) analyses performed on the compound of Example 1 as a representative of the compounds of Examples 1 to 4 are shown in FIGS. 1 to 3. In addition, the XRPD analysis was performed even after the measurement of DVS, and the result confirming that the crystalline form did not change is shown in FIG. 5.

Experimental Example 1. XRPD Assessment

The powder XRPD diffraction pattern was obtained using PANalytical X'Pert Pro MPD system equipped with a monochromatized radiation source and Ni filter as a solid-state detector by the following method.

About 20 to 30 mg of the sample was compressed in a glass sample holder so that the sample had a flat surface, the generator of the apparatus was set to 45 kV (acceleration voltage) and 40 mA (filament emission), and then, the measurement was carried out in a reflection mode (not-spin). Bragg angles (2θ) in a range of 4 to 40° were measured with the conditions of step size of 0.026° and time per step of 51 seconds.

The XRPD measurement result of the obtained crystalline form III is shown in FIG. 1.

As can be seen from the spectrum shown in FIG. 1, it was confirmed that the crystalline form III, according to the present invention, was a crystalline substance. The specific values of the XRPD are shown in Table 1 below. It was interpreted that the amorphous pattern observed at the 2θ angle of 20 to 30° was an unsolvate and due to remaining formamide.

TABLE 1

| No. | 2θ | Relative Intensity ($I/I_0$) |
|---|---|---|
| 1 | 6.238 (2) | 214.67 |
| 2 | 8.257 (1) | 236.71 |

TABLE 1-continued

| No. | 2θ | Relative Intensity ($I/I_0$) |
| --- | --- | --- |
| 3 | 8.828 (2) | 194.12 |
| 4 | 14.637 (1) | 260.93 |
| 5 | 16.618 (3) | 103.31 |
| 6 | 17.465 (2) | 241.77 |
| 7 | 18.859 (3) | 214.67 |
| 8 | 19.061 (1) | 512.65 |
| 9 | 19.333 (5) | 71.02 |
| 10 | 20.642 (3) | 137.48 |
| 11 | 22.679 (6) | 81.65 |
| 12 | 25.985 (6) | 77.96 |

Experimental Example 2. Thermogravimetric Analysis (TG/DTA)

The TG/DTA was measured using Mettler Toledo DSC1 system. About 2-5 mg of the sample is weighed, put into a 40 μL Al crucible (flat-bottomed aluminum pan with one pin-hole lid), correctly weighed, and put on a TG furnace. Then, the sample was heated to a maximum of 300° C. at a rate of 10° C./min. It was stabilized at 30° C. for 1 minute before heating. During the measurement, nitrogen gas is supplied to the inside of the instrument at a rate of 70 mL/min to prevent the inflow of oxygen and other gases. Data collection and evaluation were performed using the software STARe.

The TG/DTA measurement result of the obtained crystalline form III is shown in FIG. 2.

As can be seen in FIG. 2, for the crystalline form III, two endothermic peaks were observed at about 95.08° C. (onset) and about 216.53° C. (onset) with the weight loss of 1.2% w/w (0.17 mol, eq. formamide) and 27.9% w/w (5.4 mol. eq. formamide), respectively. Herein, the temperature values may have an error of ±5° C.

The temperature at which the endothermic peak at about 216.53° C. (onset) appears was consistent with the boiling point of formamide. In the NMR result below, formamide was also confirmed. Thus, it was confirmed that the crystalline form III was a formamide solvate.

Experimental Example 3. 1H Nuclear Magnetic Resonance (NMR) Spectrum

The result of the NMR analysis for the obtained crystalline form III using methanol d4 solvent at Bruker 500 MHz is shown in FIG. 3.

The NMR analysis result showed that the crystalline form III was the formamide solvate of formula 1.

The invention claimed is:

1. A crystalline form III of a compound of the following formula 1, a pharmaceutically acceptable salt thereof, or a solvate thereof, wherein the X-ray powder diffraction (XRPD) pattern has 5 or more characteristic peaks selected from among peaks with the following diffraction angles (2θ values) of: 6.238±0.1°, 8.257±0.1°, 8.828±0.1°, 16.618±0.1°, 17.465±0.1°, 18.859±0.1°, 19.061±0.1°, 19.333±0.1°, 20.642±0.1°, 22.679±0.1°, and 25.985±0.1°,

[Formula 1]

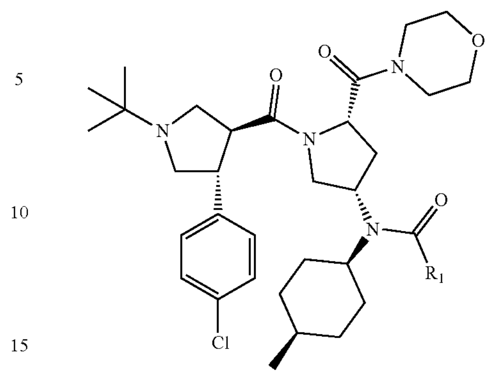

wherein $R_1$ is $C_2$-$C_5$ alkyl.

2. The crystalline form III of claim 1, wherein $R_1$ is $C_2$-$C_4$ alkyl.

3. The crystalline form III of claim 2, wherein the compound of formula 1 is selected from the group consisting of:

N-((3S,5S)-1-((3S,4R)-1-(tert-butyl)-4-(4-chlorophenyl) pyrrolidine-3-carbonyl)-5-(morpholine-4-carbonyl) pyrrolidin-3-yl)-N-((1s,4R)-4-methylcyclohexyl) isobutyramide;

N-((3S,5S)-1-((3S,4R)-1-(tert-butyl)-4-(4-chlorophenyl) pyrrolidine-3-carbonyl)-5-morpholine-4-carbonyl) pyrrolidin-3-yl)-N-((1s,4R)-4-methylcyclohexyl) propionamide; and N-((3S,5S)-1-((3S,4R)-1-(tert-butyl)-4-(4-chlorophenyl) pyrrolidine-3-carbonyl)-5-(morpholine-4-carbonyl) pyrrolidin-3-yl)-N-((1s,4R)-4-methylcyclohexyl) pivalamide.

4. The crystalline form III of claim 1, wherein the pharmaceutically acceptable salt is selected from the group consisting of: a hydrochloride, a sulfate, a nitrate, a phosphate, a hydrobromide, and a hydroiodide.

5. The crystalline form III of claim 1, which is a crystalline form of a formamide solvate of formula 1.

6. A method for preparing the crystalline form III described in claim 1, the method comprising the steps of: preparing a mixed solution by dissolving the compound of formula 1 in a crystallization solvent; and obtaining crystals from the mixed solution.

7. The method for preparing the crystalline form III of claim 6, wherein the crystals are obtained by anti-solvent crystallization.

8. The method for preparing the crystalline form III of claim 6, wherein the crystals are obtained by slurry method.

9. The method for preparing the crystalline form III of claim 6, wherein the crystallization solvent comprises a polar organic solvent.

10. The method for preparing the crystalline form III of claim 9, wherein the polar organic solvent comprises formamide, N,N-dimethylformamide, N-methyl-2-pyrrolidone, or mixtures thereof.

11. The method for preparing the crystalline form III of claim 9, wherein the crystallization solvent further comprises a non-polar organic solvent.

12. The method for preparing the crystalline form III of claim 11, wherein the non-polar organic solvent comprises hexane, heptane, cyclohexane, carbon tetrachloride, benzene, chloroform, or mixtures thereof.

13. A pharmaceutical composition comprising the crystalline form III according to claim 1 and a pharmaceutically acceptable carrier.

14. A method for agonizing the function of a melanocortin-4 receptor, the method comprising administering the crystalline form III according to claim 1 to a subject in need thereof.

15. The method of claim 14, which is for treating obesity, diabetes, or erectile dysfunction.

16. A pharmaceutical composition comprising the crystalline form III according to claim 2 and a pharmaceutically acceptable carrier.

17. A pharmaceutical composition comprising the crystalline form III according to claim 3 and a pharmaceutically acceptable carrier.

18. A pharmaceutical composition comprising the crystalline form III according to claim 4 and a pharmaceutically acceptable carrier.

19. A pharmaceutical composition comprising the crystalline form III according to claim 5 and a pharmaceutically acceptable carrier.

20. The crystalline form III of claim 1, wherein $R_1$ is ethyl, n-propyl, isopropyl, n-butyl, isobutyl, sec-butyl, or tert-butyl.

21. The crystalline form III of claim 2, wherein $R_1$ is ethyl.

22. The crystalline form III of claim 2, wherein $R_1$ is n-propyl.

23. The crystalline form III of claim 2, wherein $R_1$ is isopropyl.

24. The crystalline form III of claim 2, wherein $R_1$ is n-butyl.

25. The crystalline form III of claim 2, wherein $R_1$ is isobutyl.

26. The crystalline form III of claim 2, wherein $R_1$ is sec-butyl.

27. The crystalline form III of claim 3, wherein the compound is N-((3S,5S)-1-((3S,4R)-1-(tert-butyl)-4-(4-chlorophenyl) pyrrolidine-3-carbonyl)-5-(morpholine-4-carbonyl) pyrrolidin-3-yl)-N-((1s,4R)-4-methylcyclohexyl) isobutyramide.

28. The crystalline form III of claim 3, wherein the compound is N-((3S,5S)-1-((3S,4R)-1-(tert-butyl)-4-(4-chlorophenyl) pyrrolidine-3-carbonyl)-5-morpholine-4-carbonyl) pyrrolidin-3-yl)-N-((1s,4R)-4-methylcyclohexyl) propionamide.

29. The crystalline form III of claim 3, wherein the compound is N-((3S,5S)-1-((3S,4R)-1-(tert-butyl)-4-(4-chlorophenyl) pyrrolidine-3-carbonyl)-5-(morpholine-4-carbonyl) pyrrolidin-3-yl)-N-((1s,4R)-4-methylcyclohexyl) pivalamide.

* * * * *